(12) United States Patent
Song et al.

(10) Patent No.: US 8,487,933 B2
(45) Date of Patent: Jul. 16, 2013

(54) SYSTEM AND METHOD FOR MULTI-SEGMENT CENTER POINT TRAJECTORY MAPPING

(75) Inventors: Ting Song, Clarksburg, MD (US); Vincent B. Ho, N. Bethesda, MD (US)

(73) Assignees: General Electric Company, Schenectady, NY (US); The Henry M. Jackson Foundation for the Advancement of Military Medicine, Inc., Rockville, MD (US)

( * ) Notice: Subject to any disclaimer, the term of this patent is extended or adjusted under 35 U.S.C. 154(b) by 462 days.

(21) Appl. No.: 12/961,159

(22) Filed: Dec. 6, 2010

(65) Prior Publication Data

US 2011/0075902 A1 Mar. 31, 2011

Related U.S. Application Data

(63) Continuation-in-part of application No. 12/415,538, filed on Mar. 31, 2009.

(51) Int. Cl.
*G06T 11/20* (2006.01)
*G06K 9/00* (2006.01)

(52) U.S. Cl.
USPC .......................................... 345/440; 382/128

(58) Field of Classification Search
None
See application file for complete search history.

(56) References Cited

U.S. PATENT DOCUMENTS

| | | | |
|---|---|---|---|
| 6,310,623 B1* | 10/2001 | Zhang | 345/442 |
| 2005/0245803 A1* | 11/2005 | Glenn Jr. et al. | 600/407 |
| 2008/0077032 A1* | 3/2008 | Holmes et al. | 600/523 |
| 2009/0208078 A1* | 8/2009 | Fritz et al. | 382/130 |

OTHER PUBLICATIONS

Marwick et al., "The Future of Cardiovascular Imaging in the Diagnosis and Management of Heart Failure, Part 1: Tasks and Tools," Journal of the American Heart Association, Circulation Cardiovascular Imaging, 2008, pp. 58-69, http://circimaging.ahajournals.org/.
Goldberger et al., "Heart Rhythm Society Scientific Statement on Noninvasive Risk Stratification Techniques for Identifying Patients at Risk for Sudden Cardiac Death," American Heart Association/American College of Cardiology Foundation, vol. 52, No. 14, 2008, pp. 1179-1199.

(Continued)

*Primary Examiner* — Kee M Tung
*Assistant Examiner* — Frank Chen
(74) *Attorney, Agent, or Firm* — Ziolkowski Patent Soutions Group, SC

(57) ABSTRACT

A computer implemented method of mapping of multiple regional center point trajectory movements of cavity walls is provided in which images are acquired and a region-of-interest is identified in each of the images. The region-of-interest is divided into a plurality of distinct regions and a regional center point for each of the regions is located in the images. For each regional center point, a center point trajectory is determined based on variances in position of the center points from each other in the images. The center point trajectory of each regional center point is decomposed into radial and circumferential components so as to isolate radial component of the center point trajectory for each regional center point in each of the images and radial motion versus time curves are displayed for each regional center point based on the determined radial component for each regional center point in each of the images.

20 Claims, 16 Drawing Sheets

OTHER PUBLICATIONS

Klocke et al., "ACC/AHA/ASNC Guidelines for the Clinical Use of Cardiac Radionuclide Imaging—Executive Summary: A Report of the American College of Cardiology/American Heart Association Task Force on Practice Guidelines," Journal of the American Heart Association, Circulation, 2003, pp. 1404-1418, http://circ.ahajournals.org/.

Douglas et al., ACCF/ASE/ACEP/AHA/ASNC/SCAI/SCCT/SCMR 2008 Appropriateness Criteria for Stress Echocardiography: A Report of the American College of Cardiology Foundation Appropriateness Criteria Task Force, American Society of Echocardiography, American College of Emergency Physicians, American Heart Association, American Society of Nuclear Cardiology, Society for Cardiovascular Angiography and Interventions, Society of Cardiovascular Computed Tomography, and Society for Cardiovascular Magnetic Resonance: Endorsed by the Heart.

Tomlinson et al. "Asessment of Myocardial Viability: Comparison of Echocardiography versus Cardia Magnetic Resonance Imaging in the Current Era," Heart, Lung and Circulation, 2008, pp. 173-185.

Caiani et al., "Automated Interpretation of Regional Left Ventricular Wall Motion from Cardiag Magnetic Resonance Images," Taylor & Francis Group, LLC, Journal of Cardiovascular Magnetic Resonance, 2006, pp. 427-433.

Nesser et al., "Volumetric analysis of regional left ventricular function with real-time three-dimensional echocardiography: validation by magnetic resonance and clinical utility testing," Heart, 2007, pp. 572-578, http://heart.bmj.com/.

Sugeng et al., "Quantitative Assessment of Left Ventricular Size and Function: Side-by-Side Comparison of Real-Time Three-Dimensional Echocardiography and Computed Tomography With Magnetic Resonance Reference," American Heart Association, Circulation, 2006, pp. 654-661, http://circ.ahajournals.org/.

Sechtem et al., "Regional Left Ventricular Wall Thickening by Magnetic Resonance Imaging: Evaluation in Normal Persons and Patients with Global and Regional Dysfunction," The American Journal of Cardiology, vol. 59, 1987, pp. 145-151.

Park et al., "Assessment of left ventricular asynchrony using volume—time curves of 16 segments by real-time 3 dimensional echocardiography: Comparison with tissue Doppler imaging," The European Journal of Heart Failure, vol. 9, 2007, pp. 62-67.

Aletras et al., "DENSE: Displacement Encoding with Stimulated Echoes in Cardiac Functional MRI," Journal of Magnetic Resonance, vol. 137, 1999, pp. 247-252.

Zerhouni et al. "Human Heart: Tagging with MR Imaging—A Method for Noninvasive Assessment of Myocardial Motion," Cardiac Radiology, vol. 169, 1988, pp. 59-63.

\* cited by examiner

US 8,487,933 B2

SYSTEM AND METHOD FOR MULTI-SEGMENT CENTER POINT TRAJECTORY MAPPING

CROSS-REFERENCE TO RELATED APPLICATIONS

The present application is a continuation in-part of and claims priority to U.S. Ser. No. 12/415,538 filed Mar. 31, 2009, the disclosure of which is incorporated herein by reference.

BACKGROUND OF THE INVENTION

Embodiments of the invention relate generally to cavity wall function and, more particularly, to mapping of multiple regional center point trajectory movements of the cavity.

The assessment of ventricular wall motion is important in patients with suspected or known cardiac disease since it provides quantitative assessment of cardiac function. Ventricular wall motion evaluation is used for clinical decision-making regarding the need for more aggressive medical and/or interventional therapy such as cardiac resynchronization therapy. The non-invasive evaluation of ventricular wall motion is typically performed during rest, exercise, or while under pharmacologic stress and may be based on an imaging modality such as echocardiography, radionuclide imaging, magnetic resonance imaging (MRI), or computed tomography (CT).

Traditional assessments of wall motion during rest or stress include global parameters of left ventricular volumes and ventricular ejection fraction (EF), which is derived from ventricular volume determinations. However, it is not uncommon for patients with mild forms of cardiac disease (e.g., small myocardial infarction) to exhibit only regional wall motion abnormalities while preserving their global parameters (i.e., normal ejection fraction). Detection and quantification of regional wall motion changes are important for early disease detection, surveillance of disease progression, and/or assessment of therapeutic outcome. Regional wall motion analysis is also important for provocative cardiac function testing such as dobutamine stress testing for myocardial viability.

Regional wall motion assessment can be performed visually, but inter- and intra-observer agreement is often less than optimal and highly dependent on reader expertise and experience. More quantitative assessment of regional wall motion can be determined using computer assisted measurement of regional ejection fraction, whereby regional sub-volume ejection fractions are determined, or by measurement of segmental wall thickening. Specific imaging techniques that directly measure the movement of the myocardial wall such as tissue Doppler using echocardiography and specialized MRI pulse sequences (e.g., DENSE or myocardial tagging) are known. These echocardiographic and MR imaging techniques, however, use additional time to acquire specialized data sets and for operator-initiated image post-processing. Some of these quantitative methods can track changes over time and can be used to determine intra- or inter-ventricular mechanical dyssynchrony. Despite the large number of available methods, however, visual assessment (i.e., a qualitative method) of wall motion is still the most widely used, but its application is heavily reliant on observer experience and expertise. Quantitative methods such as those described above are associated with a variety of limitations including prolonged image acquisition times, high observer interactive time and expertise requirements, inherently high spatial and/or temporal resolution requirements, and/or high imaging data/processing requirements.

It would therefore be desirable to have an apparatus and method capable of quantitatively assessing cavity wall motion efficiently while reducing variations in observer-based assessments. It would further be desirable for such an apparatus and method to be capable of quantitatively assessing the motion of multiple discrete wall segments in a simultaneous fashion, so as to enable separate analysis of each discrete wall segment and analysis of wall motions relative to one another.

BRIEF DESCRIPTION OF THE INVENTION

According to an aspect of the invention, a non-transitory computer readable storage medium includes a computer program comprising instructions, which when executed by a computer, cause the computer to acquire a plurality of images, identify a region-of-interest in each of the plurality of images, divide the region-of-interest into a plurality of distinct regions, and locate a regional center point for each of the plurality of regions in each of the plurality of images. The instructions further cause the computer to determine, for each regional center point, a center point trajectory based on variances in position of the center points from each other in the plurality of images, decompose the center point trajectory of each regional center point into radial and circumferential components so as to isolate radial component of the center point trajectory for each regional center point in each of the plurality of images, and based on the determined radial component for each regional center point in each of the plurality of images, display radial motion versus time curves for each regional center point.

According to another aspect of the invention, a method for multi-segment chamber movement analysis includes obtaining a plurality of images of a region-of-interest including a chamber therein, dividing the chamber into a plurality of segments for each of the plurality of images, and locating a centroid of each segment of the chamber in each of the plurality of images. The method also includes tracking movement of the centroid in each respective segment across the plurality of images to determine a center point trajectory for each centroid, determining a radial motion for the centroid in each respective segment based on the center point trajectory, and displaying the radial motion for each centroid in each the plurality of images on a respective radial motion versus time curve.

According to yet another aspect of the invention, a non-transitory computer readable storage medium includes a computer program comprising instructions, which when executed by a computer, cause the computer to obtain a plurality of images of a region-of-interest including a walled chamber therein, isolate the walled chamber in each of the plurality of images, divide the walled chamber into a plurality of segments for each of the plurality of images, and locate a regional center point of each of plurality of segments in each of the plurality of images. The instructions further cause the computer to determine, for each of the regional center points, a center point trajectory based on a positional relationship of the center points to each other in the plurality of images, determine a radial motion component of the center point trajectory for each of the regional center points in each of the plurality of images, and display the radial motion for each regional center point in each of the plurality of images on a respective radial motion versus time curve.

Various other features and advantages will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION

Figure 1:
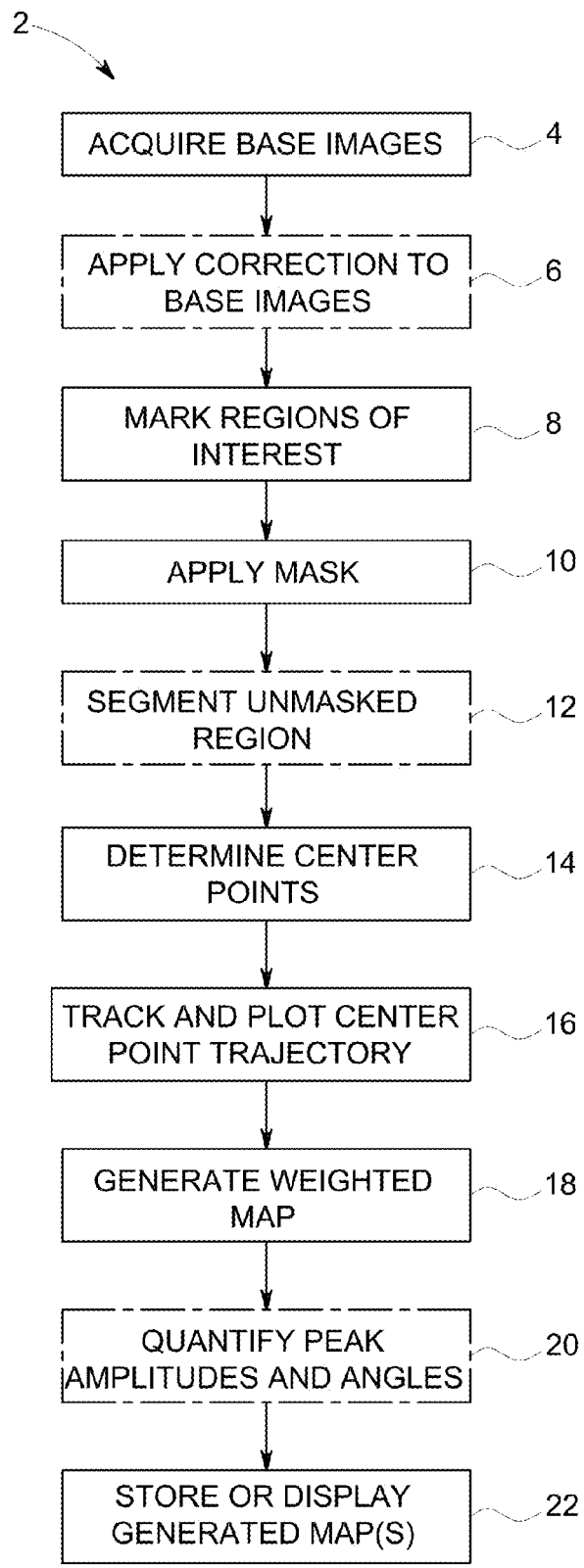
FIG. 1 is a flowchart illustrating a technique for center point trajectory mapping according to an embodiment of the invention.

FIG. 1 shows a technique 2 for center point trajectory mapping according to an embodiment of the invention. The technique 2 may be used to quantify center point trajectory of a cavity. A composite of cavity wall motion, such as ventricular wall motion of a heart, can be summarized during the various cardiac phases of the heart in the movement of the center point of the ventricular chamber throughout the cardiac phases. Technique 2 includes the tracking of the cavity center point over time. In this manner, quantitative measurements such as pattern, angle, and amplitude for regional as well as global wall motion abnormalities may be determined. Changes in center point pattern, angle, and amplitude can be used to assess myocardial response during exercise (e.g., treadmill or hand grip), during pharmacology (e.g., dobutamine or adenosine) stress testing, or following therapeutic intervention (e.g., medication regimen or percutaneous coronary intervention).

Figure 2:
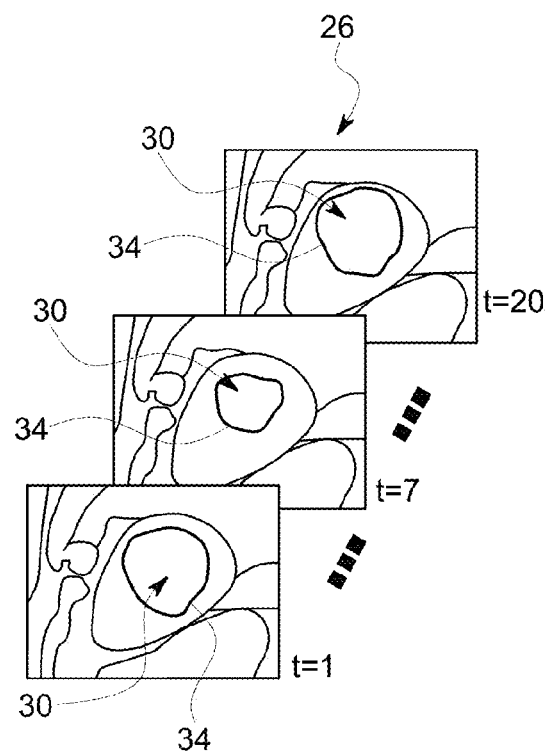
FIGS. 2-4 are schematic diagrams graphically illustrating a portion of the steps of the technique of FIG. 1 according to an embodiment of the invention.

Referring to FIGS. 1 and 2, technique 2 includes acquiring a plurality of base images 26 (shown in FIG. 2) at block 4. Acquiring the base images 26 may include performing an imaging scan and reconstructing images from the imaging scan or may include acquiring stored images previously reconstructed. Acquiring stored images allows quantification of center point trajectory movement of a patient without having to re-scan the patient. According to an embodiment of the invention, the base images may be from any imaging modality. For example, the base images may include echocardiography images, radionuclide imaging images, magnetic resonance images, computed tomography images, x-ray images, or ultrasound images. In addition, the base images may be based on any type of scanning sequence or imaging parameter setup. In an embodiment, the plurality of base images are ordered in a consecutive or chronological series of images. For example, cardiac images of a patient may sequentially illustrate ventricular wall motion through a full cardiac cycle (e.g., through the systole and diastole phases). As shown in FIG. 2, images 26 are chronologically ordered and represent twenty, two-dimensional images acquired during a full cardiac cycle. The base images 26 at block 4 may be two-dimensional images or three-dimensional images acquired from an image storage database or acquired in real time. Acquiring images from an image storage database allows any patient images to be used whether the images were recently acquired or were acquired weeks, months, or even years beforehand.

Referring to FIG. 1, a correction may be applied to the base images 26 at block 6 to remove any artifacts that may be present. For example, if the base images are MR images, an inhomogeneity correction may be applied to the base images to correct inhomogeneity artifacts. Other types of corrections may also be applied (e.g., based on the type of imaging modality used to generate the base images) and are contemplated herein. It is also contemplated that a correction may not be applied to the base images if desired. Accordingly, block 6 is shown with dashed lines and may be removed from technique 2 according to an embodiment of the invention.

Referring to FIGS. 1 and 2, a region of interest (ROI) is marked in each of the base images at block 8. The ROIs may be, for example, the left ventricle of a patient's heart as shown in FIG. 2. ROI marking includes delineating a border 34 of a cavity 30 of the ROI in each of the base images 26. ROI marking may include automatically marking the cavities 30 using connected pieces based on signal intensity values of the cavities 30 in the base images. In addition or alternatively thereto, a user may select the respective cavities 30 via computer-aided input.

Figure 3:
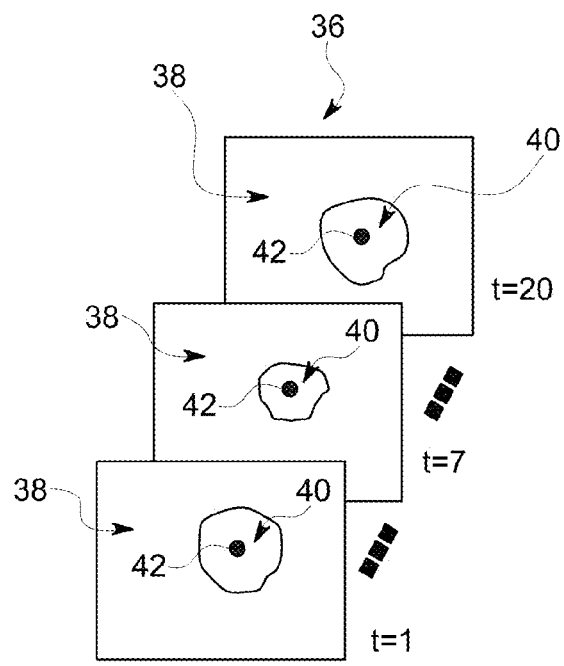

Referring to FIGS. 1 and 3, at block 10, a mask is applied to each of the base images 26 (shown in FIG. 2). The masks are configured to mask the portions of the base images outside of the delineated border 34 and convert the images into binary mask images 36. FIG. 3 illustrates a masked portion 38 of images 36 masking a region outside the delineated borders 34 of images 26. An unmasked portion 40 of images 36 corresponds to a region inside the delineated borders 34 of images 26.

According to an embodiment of the invention, the unmasked portions 40 of binary mask images 36 may be segmented at block 12 (shown in dashed lines). Segmenting an ROI into multiple segments allows for a more detailed or focal analysis within each ROI as may be desired for a higher spatial definition of movement.

A center point or centroid 42, which is the geometric center of the shape of the unmasked portions 40, is determined or calculated for each unmasked portion 40 or segmented portion in the binary mask images 36 at block 14. According to an embodiment of the invention, calculated center points 42 from the binary mask images 36 are used for center point tracking.

Figure 4:
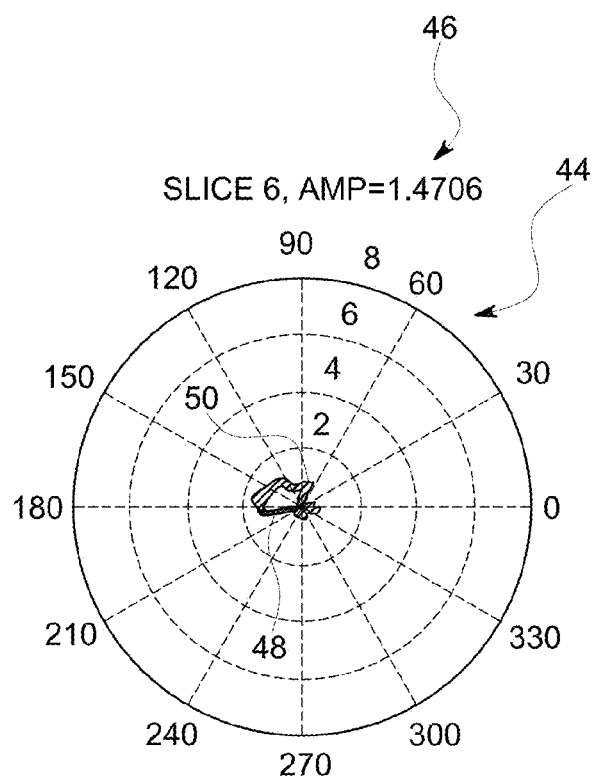

Referring to FIGS. 1, 3, and 4, trajectories of the center points 42 between consecutive images 36 are tracked and plotted at block 16. Tracking of the center point trajectories includes determining the differences in center point positions between the respective consecutive images 36. These differences identify an amplitude of center point movement and an angle of center point movement. Plotting of the center point trajectories includes plotting the distances (amplitudes) and directions (angles) of center point trajectory movement on a polar coordinate map 44. Polar coordinate map 44 shown in FIG. 4 is an absolute center point displacement map showing raw or absolute values for the center point trajectory data. The plotting of amplitudes and angles of center point movement on the map illustrates, for example, the degree of wall motion abnormality and the location indicated by direction in both systolic and diastolic phases of a cardiac phase. The plotting of amplitudes and angles of center point movement on the map also illustrates center point trajectory patterns useful in diagnoses.

Referring to FIG. 1, post-processing of map data includes generating a weighted center point displacement map at block 18 based on the absolute center point displacement map created at block 16. In one embodiment, the weighted center point displacement map is an ejection fraction (EF) weighted center point displacement map that is generated by calculating a local EF value based on the base images and dividing the absolute center displacement by the local EF value. In this manner, a quantitative tool for assessment and surveillance of patients with diffuse wall motion abnormalities may be generated. For example, a patient with global heart disease may have small absolute displacement as identified on the absolute center point displacement map, but the EF will be low. Accordingly, the ejection fraction weighted center point displacement map may be used to assess and quantify issues related to ejection fraction.

In another embodiment, the weighted center point displacement map is a chamber radius change weighted center point displacement map useful for global cardiac motion evaluation that is generated by calculating a difference between a maximum radius of the ROIs and a minimum radius of the ROIs among all the images (e.g., in the whole cardiac cycle) and dividing absolute center point displacement by the calculated difference. As such, an additional quantitative tool for assessment and surveillance of patients is provided.

Referring to FIGS. 1 and 4, in an embodiment of the invention, post-processing of map data also includes identifying a peak or maximum amplitude 46 of center point movement in the absolute or weighted center point displacement maps and displaying the peak amplitude 46 with its respective map at block 20 (shown with dashed lines). The peak amplitude 46 represents the largest distance difference between the beginning or first center point and any of the other center points. In addition, the number of the image or slice where the peak amplitude occurs may be identified and displayed. Furthermore, it is contemplated that a peak or maximum angle may also be identified and displayed based on a largest angular difference between the first center point and any of the other center points.

As shown in FIG. 4, a peak amplitude of 1.4706 has been identified from the data in map 44 and is displayed, while the slice number (six) where the peak amplitude occurs has also been identified and displayed. The time point of peak amplitude in this case corresponds to the time point of end-systole and can serve as a measure of degree wall motion defect not only in terms of amplitude and angle but also time. Identification of the maximum amplitude of center point movement in this manner allows for computer-related quantification and reduces guessing introduced by visual assessment.

The absolute or weighted center point displacement maps and their related data generated at blocks 18-22 may be stored for later use or displayed to a user on a display at block 22. According to an embodiment of the invention, the map display includes color-coding separate portions of center point movement among the ROIs. For example, movement of the center points during a systolic phase 48 (shown in FIG. 4 and similarly labeled in FIGS. 6-10) of a cardiac cycle may be displayed in one line style and/or color such as red, and movement of the center points during a diastolic phase 50 (shown in FIG. 4 and similarly labeled in FIGS. 6-10) of the cardiac cycle may be displayed in another line style and/or color such as blue. In this manner, motion abnormality in the two phases can be uncoupled.

Besides amplitudes and angles, the pattern of the trajectory is also useful. For example, the shape or the pattern of the trajectory can be used for dyssynchrony evaluation. That is, the distance between the systolic phase 48 and the diastolic phase 50 indicate a degree of dyssynchronization. In general, the wider the distance between systolic and diastolic trajectories, the more the possibility of a dyssynchronized cardiac motion exists.

Figure 5:
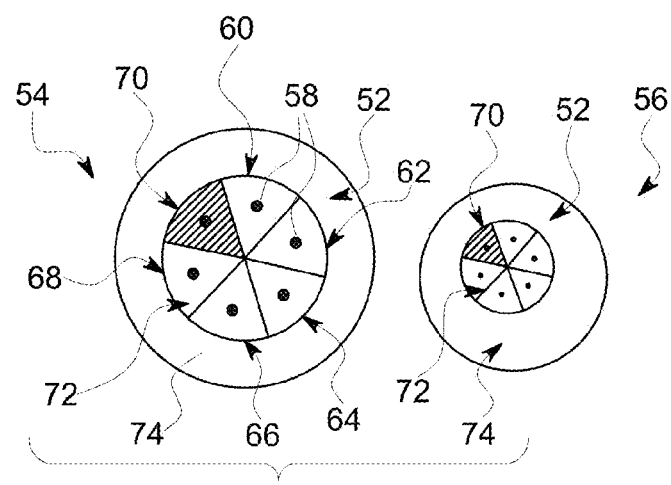
FIG. 5 is a schematic representation of a segmented ROI showing center points for each ROI segment according to an embodiment of the invention.

FIG. 5 is a schematic representation of a segmented ROI showing center points for each ROI segment according to an embodiment of the invention. In FIG. 5, a segmented ROI 52 of two cardiac phases 54, 56 is shown that shows center points 58 for each ROI segment 60, 62, 64, 66, 68, 70 according to an embodiment of the invention. Segmenting an ROI into multiple local segments 60-70 allows for a more detailed or focal analysis within each ROI as may be desired for a higher spatial definition of movement. Segmented ROI 52 may be identified and segmented according to that described above in FIG. 1 with respect to blocks 4-16. Cardiac phase 54 illustrates a relaxed state and includes a chamber 72 surrounded by cardiac muscle 74, which is shown having a uniform thickness about chamber 72. ROI segments 60-70 are distributed throughout chamber 72. In cardiac phase 56, a contracted state (i.e., end-systole) is illustrated. Cardiac phase 56 illustrates that the segmented ROI 52 is shifted in the direction of ROI segment 70. Accordingly, the direction of abnormal wall motion is also in the direction of ROI segment 70. While FIG. 5 shows six segments in segmented ROI 52, it is contemplated that any number of segments may be used. By comparing regional center point trajectories, relative time points for peak amplitude can be compared for determination of ventricular dyssynchrony (i.e., the condition in which ventricular wall motion is no longer synchronous in the time domain). In addition to comparing regional center point trajectories, the global center point trajectories of the left and right ventricles (or of any other chambers) may also be compared to determine cardiac dyssynchrony in the time domain as well as in their relative motions. In this manner, a comparison of regional or global center point trajectory over time will enable the quantification and assessment of changes in amplitude over time, differences in trajectory arc over time, and changes in trajectory pattern over time between various time points.

Figure 6:
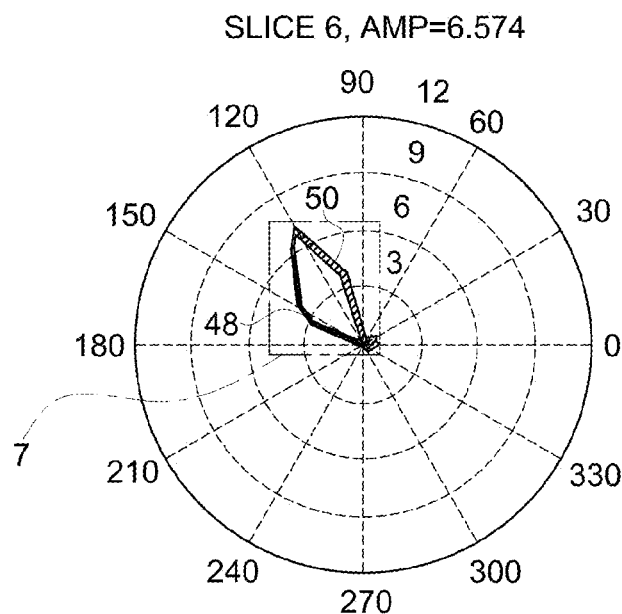
FIGS. 6 and 7 illustrate exemplary polar maps showing center point movement of a patient with an acute myocardial infarction of the anteroseptal wall of the left ventricle according to an embodiment of the invention.
Figure 7:
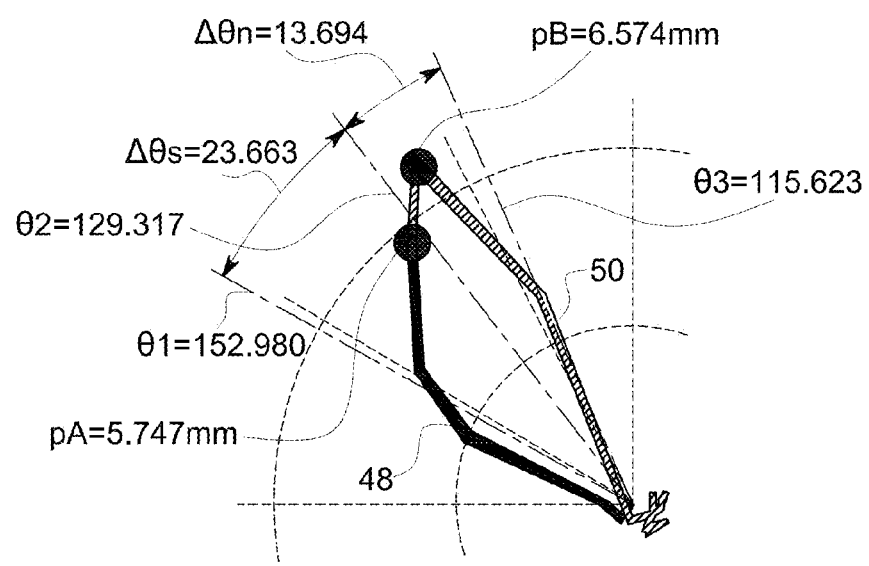

Abnormal wall motion is determined by high amplitude (e.g., greater than 3.0) of absolute movement of the center point towards the region of abnormal wall motion. FIGS. 6 and 7 are examples of movement of the center point shown in polar maps of a patient with an acute myocardial infarction of the anteroseptal wall of the left ventricle for illustrative purposes according to one embodiment of the invention. FIG. 7 shows a close-up of the polar map of FIG. 6 about line 7-7. According to an embodiment of the invention, angles and amplitudes relevant to the polar map may be quantified and shown. A series of angles θ1, θ2, and θ3 are quantified and displayed as well as a difference between θ2 and θ1 (Δθs=θ2−θ1) and a difference between θ3 and θ2 ($\Delta\theta_D$=θ3−θ2), where Δθs is an angle of trajectory during systolic contraction (i.e., systole), and $\Delta\theta_D$ is an angle of trajectory diastolic relaxation (i.e., diastole) of the left ventricle. After end of systolic phase 48 where there is a minimal chamber volume, an amplitude ρ at point A is 5.747 mm. When the amplitude ρ reaches the peak at point B, it is in diastolic phase 50. The shapes of the systolic and diastolic phases 48, 50 indicate that wall motion is not synchronized as there is increased amplitude of the center point despite the overall chamber volume reaching a minimum (i.e., end-systole). The width of the arcs, Δθs, ΔθD, and Δθs+ΔθD=37.357°, are also indicators of how dyssynchronized the motion is. The angle and amplitude of the center point trajectory can be used to follow left ventricular remodeling and functional recovery over time. As shown in FIGS. 6 and 7, a peak amplitude, a trajectory direction, a trajectory pattern, and a trajectory temporal arc corresponding to center point movement over time may be quantified according to embodiments of the invention.

Figure 8:
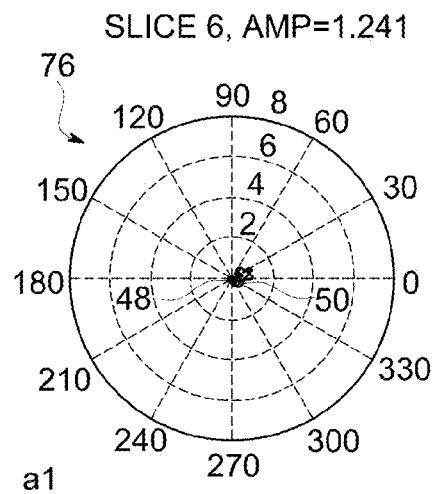
FIG. 8-10 illustrates polar map quantification examples according to an embodiment of the invention.
Figure 8:
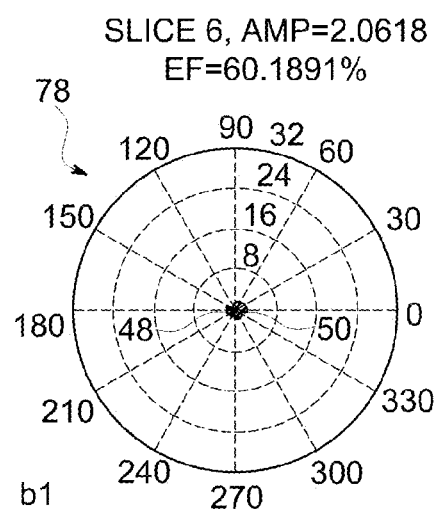
Figure 8:
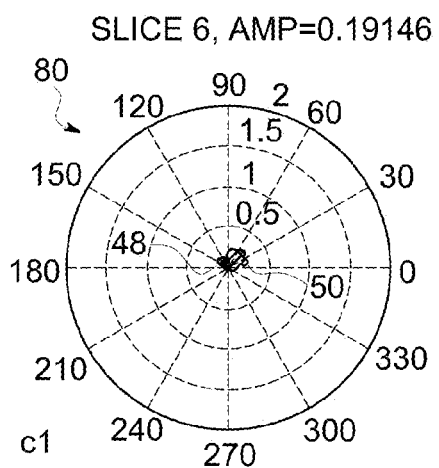
Figure 9:
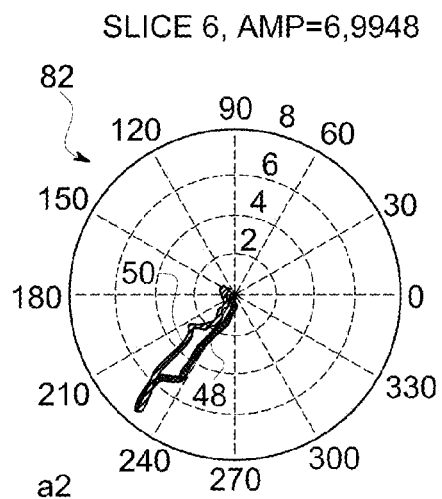
Figure 9:
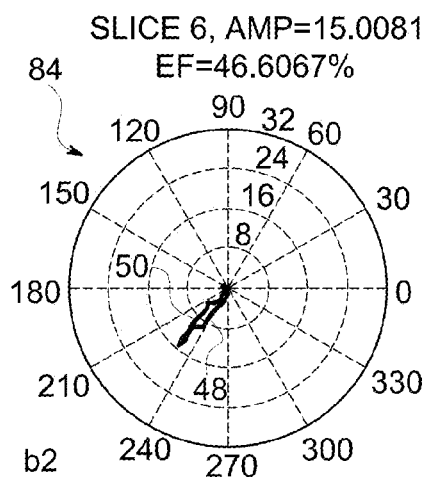
Figure 9:
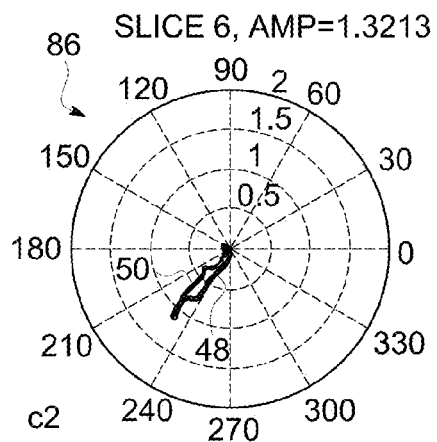
Figure 10:
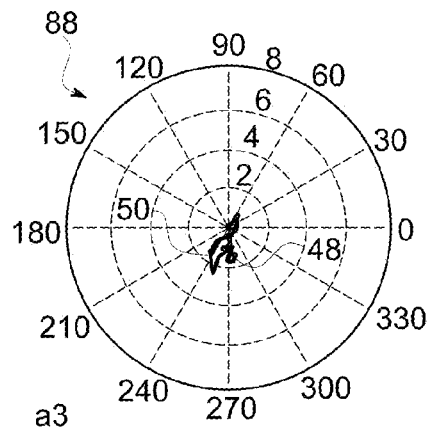
Figure 10:
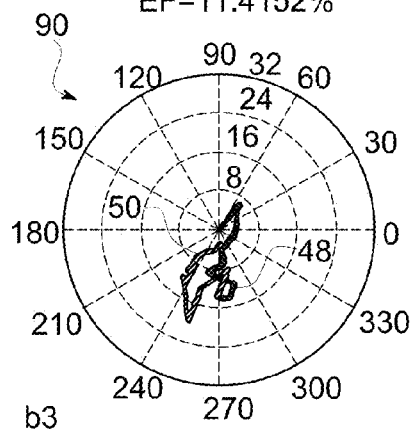
Figure 10:
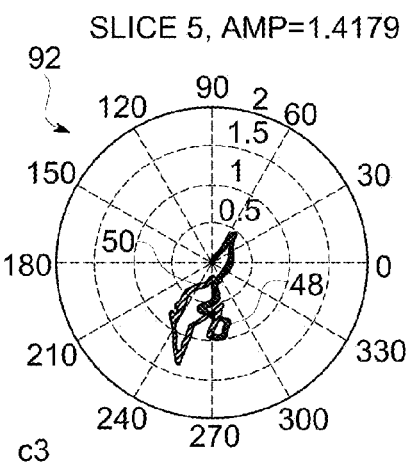

FIGS. 8-10 illustrates polar map quantification examples according to an embodiment of the invention. Maps 76, 78, and 80 respectively illustrate absolute (or raw), EF weighted, and chamber radius change weighted displacement center point maps of a healthy left ventricle. Maps 82, 84, and 86 respectively illustrate absolute (or raw), EF weighted, and chamber radius change weighted displacement center point maps of a left ventricle with hypokinesis in the inferoseptal wall. Maps 88, 90, 92 respectively illustrate absolute (or raw), EF weighted, and chamber radius change weighted displacement center point maps of a left ventricle with global hypokinesis. Absolute center point map 76 displays low amplitude movement of the center point trajectory. On EF weighted map 78 and radius change weighted map 80, low or little amplitude movement of the respective center point trajectories for the healthy left ventricle are shown. In maps 82-86, the amplitude movement is substantially larger than that shown in maps 76-80. As stated above, maps 88-92 show maps of a left ventricle with global hypokinesis. Although in absolute displacement generate weighted map 88 the amplitude movement is less than 3.0, the EF map 90 and the chamber radius weighted map 92 show that there is a substantial deviation of the center points that can be measured in pattern, angle, and amplitude. Accordingly, it can be understood that the EF and radius change weighted maps provide extra information for diagnosis for both regional and global wall motion abnormalities in addition to the information of the absolute map.

Figure 11:
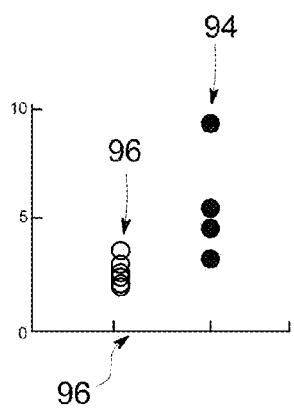
FIG. 11 illustrates exemplary plots of patient data using Welch two-sample t-test according to an embodiment of the invention.
Figure 11:
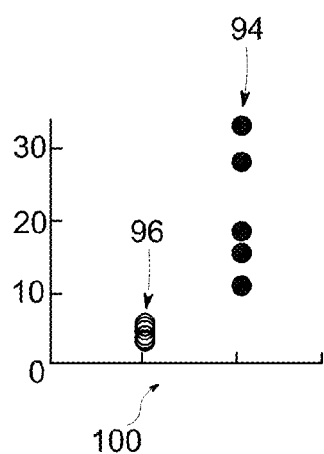
Figure 11:
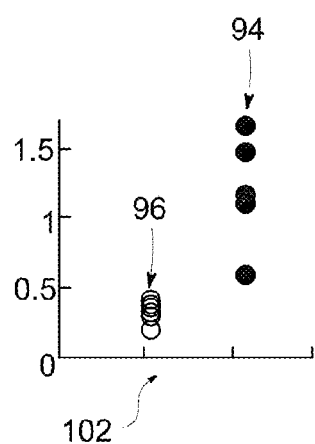

FIG. 11 illustrates plots of patient data using Welch two-sample t-test. A first group of patient data 94 for patients with mild to severe global hypokinesis is illustrated together with a second group of patient data 96 for healthy subjects. A first plot 98 illustrates data related to absolute amplitudes as quantified according to an embodiment of the invention. As illustrated, the patient data 88 for the healthy subjects all have amplitudes below five. The patient data 86 for patients with hypokinesis, however, have mixed amplitudes—including amplitudes also below 5.0. Accordingly, setting a diagnosis threshold based solely on the absolute amplitude center point trajectories may not separate the healthy subjects from all the patients with mild to severe global hypokinesis.

A second plot 100 and a third plot 102 respectively illustrate data related to EF weighted amplitudes and to chamber radius change weighted amplitudes as quantified according to an embodiment of the invention. The data 88 for healthy subjects in plots 100, 102 are shown more separated from the data 86 for subjects with such as, for example, 10.0 and 0.5, respectively, for the EF weighted plot 100 and the chamber radius change weighted plot 102 may improve accuracy in diagnosing patients with wall motion abnormalities.

Figure 12:
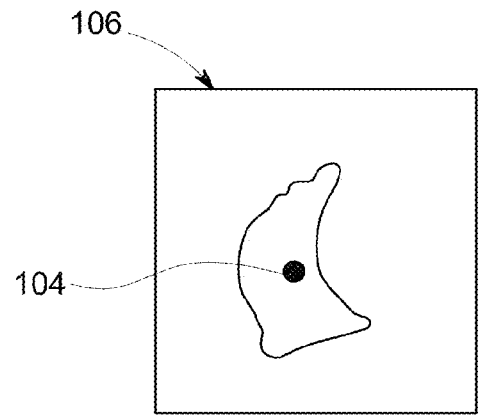
FIG. 12 illustrates a right ventricle ROI binary mask image according to an embodiment of the invention.

FIG. 12 illustrates a right ventricle ROI binary mask image according to an embodiment of the invention. In FIG. 12, a center point 104 is shown that was calculated for a right ventricle ROI in a binary mask image 106 of a patient's heart. The technique as described above may be used to track the center points of images for other cardiac chambers (e.g., the right ventricle (as shown in FIG. 12), the left atrium, the right atrium). The technique described above may also be used to track center points for ROIs of other hollow chambers such as an esophagus or a stomach of an imaging subject. In addition, it is contemplated that the ROIs may be of any cavity of an imaging subject or object in either a medical or a non-medical setting. Furthermore, the desired ROI cavity may have an irregular shape as illustrated in FIG. 12.

As described above, the base images having the desired ROIs may include images selected from any type of modality including: echocardiography images, radionuclide imaging images, magnetic resonance images, computed tomography images, x-ray images, or ultrasound images based on any type of scanning sequence or imaging parameter setup. It is contemplated that diagnosis of wall motion abnormalities can include the quantification of cavity wall motion abnormalities from one modality compared with the quantification of the cavity wall motion abnormalities from a different modality. Further, as center point measurements are quantitative, direct comparison of wall motion between different patients is also contemplated.

Figure 13:
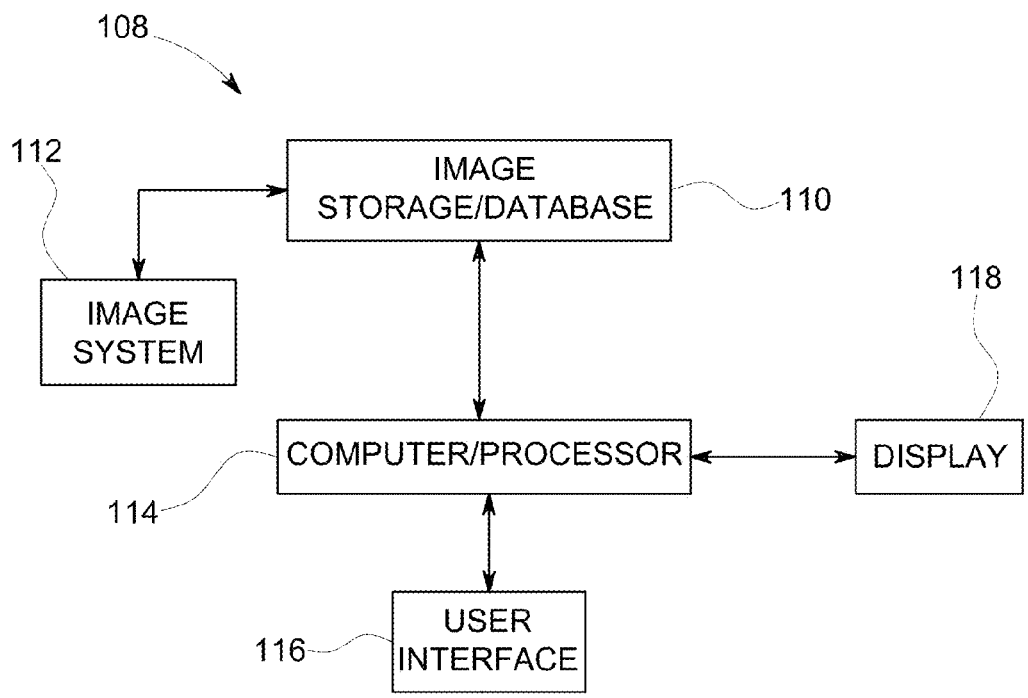
FIG. 13 is a schematic block diagram of an exemplary system incorporating an embodiment of the invention.

FIG. 13 is a schematic block diagram of an exemplary system 108 incorporating an embodiment of the invention as an example. System 108 includes an image storage or database 110 configured to store images received from an imaging system 112, for example. According to embodiments of the invention, imaging system 112 is a system capable of imaging an object via any type of modality including magnetic resonance imaging, computed tomography imaging, x-ray imaging, ultrasound imaging, or the like. In addition, images generated by imaging system 112 and stored in image database 110 may be based on any type of scanning sequence or imaging parameter setup A computer or processor 114 is programmed based on embodiments of the invention such as technique 2 described above with respect to FIG. 1. A user interface 116 allows the computer/processor 114 to receive user instructions such as instructions regarding which images to acquire from database 110 and instructions regarding choosing of the ROI cavities as described above, for example. A display 118 coupled to computer/processor 114 visually depicts any polar maps generated from the images via the computer/processor 114. Additionally, the computer/processor 114 may be programmed to quantify, compare, and display regional or global center point trajectory changes in amplitude over time, differences in trajectory arc over time, and changes in trajectory pattern over time between various time points.

Figure 14:
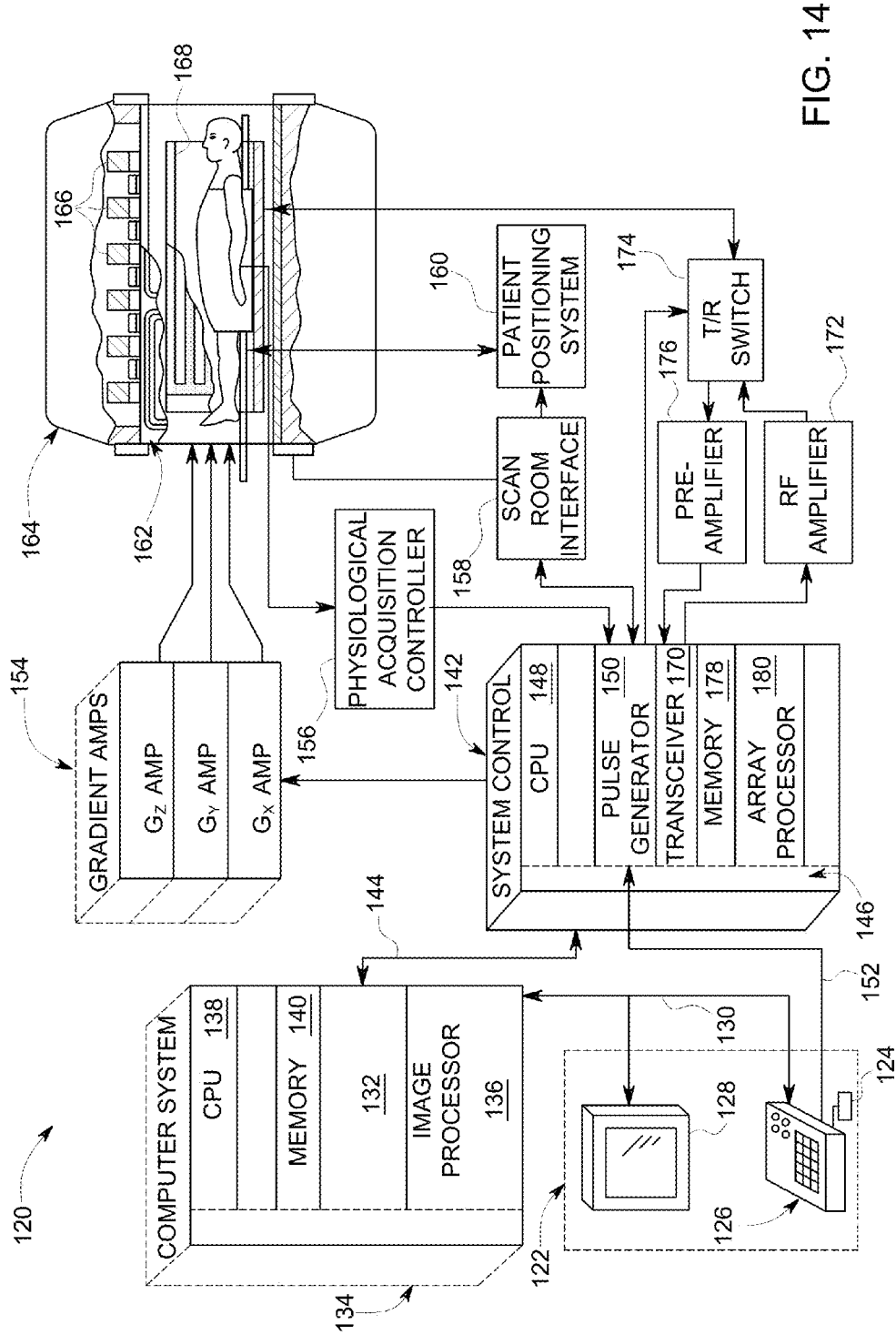
FIG. 14 is a schematic block diagram of an exemplary MR imaging system incorporating an embodiment of the invention.

While embodiments of the invention include acquiring images from any of a multiple of imaging modalities, FIG. 14 illustrates the major components of a magnetic resonance imaging (MRI) system 120 incorporating an embodiment of the invention as an example. The operation of the system 120 is controlled from an operator console 122, which includes a keyboard or other input device 124, a control panel 126, and a display screen 128. The console 122 communicates through a link 130 with a separate computer system 132 that enables an operator to control the production and display of images on the display screen 128. The computer system 132 includes a number of modules which communicate with each other through a backplane 134. These include an image processor module 136, a CPU module 138 and a memory module 140 that may include a frame buffer for storing image data arrays. The computer system 132 communicates with a separate system control 142 through a high speed serial link 144. The input device 124 can include a mouse, joystick, keyboard, track ball, touch activated screen, light wand, voice control, or any similar or equivalent input device, and may be used for interactive geometry prescription.

The system control 142 includes a set of modules connected together by a backplane 146. These include a CPU module 148 and a pulse generator module 150 which connects to the operator console 122 through a serial link 152. It is through link 152 that the system control 142 receives commands from the operator to indicate the scan sequence that is to be performed. The pulse generator module 150 operates the system components to carry out the desired scan sequence and produces data which indicates the timing, strength and shape of the RF pulses produced, and the timing and length of the data acquisition window. The pulse generator module 150 connects to a set of gradient amplifiers 154, to indicate the timing and shape of the gradient pulses that are produced during the scan. The pulse generator module 150 can also receive patient data from a physiological acquisition controller 156 that receives signals from a number of different sensors connected to the patient, such as ECG signals from electrodes attached to the patient. And finally, the pulse generator module 150 connects to a scan room interface circuit 158 which receives signals from various sensors associated with the condition of the patient and the magnet system. It is also through the scan room interface circuit 158 that a patient positioning system 160 receives commands to move the patient to the desired position for the scan.

The gradient waveforms produced by the pulse generator module 150 are applied to the gradient amplifier system 154 having Gx, Gy, and Gz amplifiers. Each gradient amplifier excites a corresponding physical gradient coil in a gradient coil assembly generally designated 162 to produce the magnetic field gradients used for spatially encoding acquired signals. The gradient coil assembly 162 forms part of a resonance assembly 164 which includes a polarizing magnet 166 and a whole-body RF coil 168. A transceiver module 170 in the system control 142 produces pulses which are amplified by an RF amplifier 172 and coupled to the RF coil 168 by a transmit/receive switch 174. The resulting signals emitted by the excited nuclei in the patient may be sensed by the same RF coil 168 and coupled through the transmit/receive switch 174 to a preamplifier 176. The amplified MR signals are demodulated, filtered, and digitized in the receiver section of the transceiver 170. The transmit/receive switch 174 is controlled by a signal from the pulse generator module 150 to electrically connect the RF amplifier 172 to the coil 168 during the transmit mode and to connect the preamplifier 176 to the coil 168 during the receive mode. The transmit/receive switch 174 can also enable a separate RF coil (for example, a surface coil) to be used in either the transmit or receive mode.

The MR signals picked up by the RF coil 168 are digitized by the transceiver module 170 and transferred to a memory module 178 in the system control 142. A scan is complete when an array of raw k-space data has been acquired in the memory module 178. This raw k-space data is rearranged into separate k-space data arrays for each image to be reconstructed, and each of these is input to an array processor 180, which operates to Fourier transform the data into an array of image data. This image data is conveyed through the serial link 144 to the computer system 132 where it is stored in memory. In response to commands received from the operator console 122, this image data may be archived in long term storage or it may be further processed by the image processor 136 and conveyed to the operator console 122 and presented on the display 128.

The computer system 132 is programmed to quantify and display maps of center point trajectory movement as described above according to an embodiment of the invention. The computer system 132 may retrieve stored images from historical scans or may acquire images during a scan followed thereafter by quantification of center point trajectories and map generation and display as described above according to an embodiment of the invention.

According to another embodiment of the invention, rather than using center point trajectory mapping to determine/indicate global wall motion, it is envisioned that the technique for center point trajectory mapping can be extended and modified so as to enable the simultaneous evaluation of multiple discrete wall segments. That is, a multi-segment center point trajectory (CPT) mapping technique is set forth for evaluation of discrete wall segments of a subject, with each discrete wall segment having a regional center point whose trajectory is mapped. In this context, the multi-segment CPT mapping technique enables separate analysis of the regional center point trajectory in each region and also provides for conclusions/diagnoses to be made based on the relationship between the regional center point trajectory of each region.

According to an exemplary embodiment, the multi-segment CPT mapping technique is employed to enable multi-segment cardiac chamber movement analysis for evaluation of discrete myocardial segments, such as in the territories/regions of the left anterior descending (LAD), right coronary artery (RCA), and left circumflex coronary artery (LCX) of the heart. The ventricular center point for each of the LAD, RCA, and LCX vascular regions is tracked over time, with the multi-segment CPT mapping technique enabling separate analysis in each coronary artery related region. The multi-segment CPT mapping technique can thus provide a quantitative and/or relative criterion of coronary artery disease related analysis and provide an indication of coronary artery disease in each specific branch.

Figure 15:
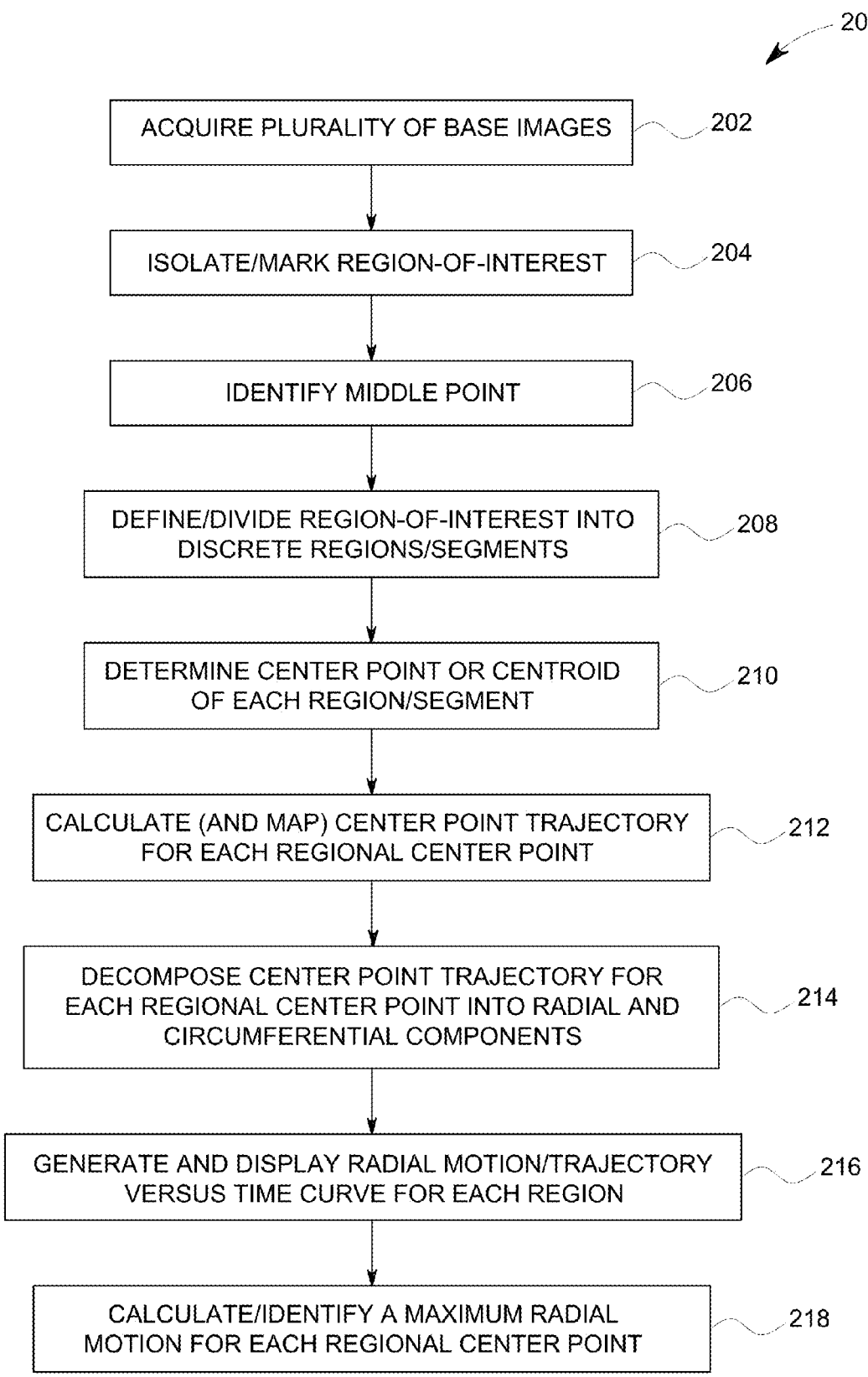
FIG. 15 is a flowchart illustrating a technique for multipoint center point trajectory mapping according to an embodiment of the invention

Referring to FIG. 15, a multi-segment CPT mapping technique 200 is displayed according to an embodiment of the invention for purposes of quantifying wall motion of discrete wall segments/regions of a walled hollow chamber. According to an exemplary embodiment, such a chamber may be a left ventricle, with the multi-segment CPT mapping technique 200 being applied to quantify wall motion of myocardial segments (i.e., left ventricular wall segments). The technique 200 begins with acquiring a plurality of base images at block 202. Acquiring the base images may include performing an imaging scan and reconstructing images from the imaging scan or may include acquiring stored images previously reconstructed. Acquiring stored images allows quantification of center point trajectory movement of a patient without having to re-scan the patient. According to an embodiment of the invention, the base images may be from any imaging modality. For example, the base images may include echocardiography images, radionuclide imaging images, magnetic resonance images, computed tomography images, x-ray images, or ultrasound images. In addition, the base images may be based on any type of scanning sequence or imaging parameter setup. In an embodiment, the plurality of base images is ordered in a consecutive or chronological series of images. For example, cardiac images of a patient may sequentially illustrate ventricular wall motion through a full cardiac cycle (e.g., through the systole and diastole phases).

Figure 16:
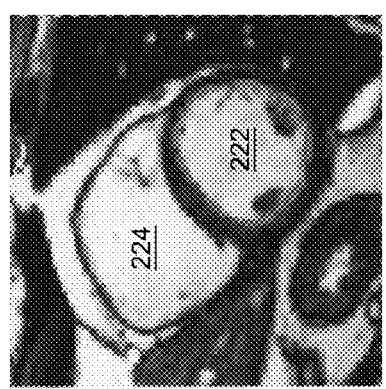

Referring to FIGS. 15 and 16, a region-of-interest (ROI), in the form of a walled, hollow chamber, is isolated and marked in each of the base images at block 204 for which wall motion analysis is desired. According to one embodiment, a segmentation is performed at block 204 to isolate the ROI from, for example, other cavities or chambers present in the images, although other methods such as image masking could also be employed. As shown in FIG. 16, for example, where the ROI encompasses the left ventricle of a patient, endocardium segmentation is performed so as to segment the left ventricle from the right ventricle and other cardiac chambers in the base images, as indicated by marking line 220 that marks the left ventricle 222 and separates it from the right ventricle 224. In performing the endocardium segmentation, it is recognized that any of a variety of systems or methods for chamber segmentation may be employed. Upon completion of the endocardium segmentation, a reference point between the segmented left ventricle 222 and right ventricle 224 is determined at block 206 (FIG. 15). That is, as shown in FIG. 16, a reference point 226, defined as the middle point between two hinged points 228, 230 of the segmented left ventricle 222 and right ventricle 224, is determined.

Figure 17:
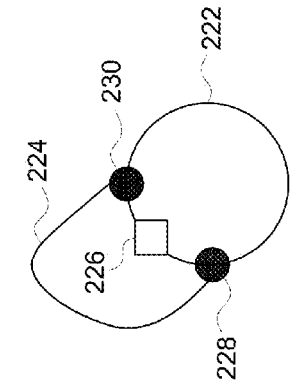

The identification/determination of the reference point 226 between the left and right ventricles 222, 224 provides for a dividing of the ROI (i.e., the left ventricle) into distinct regions/territories at block 208. According to one embodiment, the left ventricle is divided into the LAD, RCA and LCX vascular regions/territories and the corresponding ventricular well segment associated therewith. As shown in FIG. 17, the reference point 226 between the left ventricle and right ventricle is connected to the center 231 of the left ventricle chamber 222 via division line 232 to divide the LAD region 234 and the RCA region 236. Based on an embodiment of the invention where the ventricular wall is segmented into three distinct regions, the division line 232 is then rotated 120 degrees clockwise from its original position to define the LAD region 234. The division line 232 is then rotated 120 degrees counterclockwise from its original position to define the RCA region 236. Upon defining of the LAD region 234 and the RCA region 236, the remaining area of the chamber 222 is then defined as the LCX region 238. While FIG. 17 illustrates the selection of three distinct regions (i.e., the LAD, RCA and LCX regions 234, 236, 238) for wall motion analysis, it is recognized that a greater number of regions could also be selected for analysis. For example, six regions could be selected/segmented from the ventricular wall of the patient heart for wall motion analysis. In such an embodiment, it is recognized that the division/defining of the regions would vary from that which is described above in that division line 232 would be rotated by a different angular amount. For division of the ventricular wall into six distinct regions, division line 232 would be rotated clockwise/counterclockwise in 60 degree increments to define the regions. While division of the ROI into LAD, RCA and LCX vascular regions/territories is discussed above, it is noted that the actual vessel supplying the myocardium may vary and, as such, attribution of vascular territory can also be varied to match a patient's specific coronary artery anatomy. Therefore, embodiments of the invention are not limited to the specific vascular territories set forth above.

Figure 18:
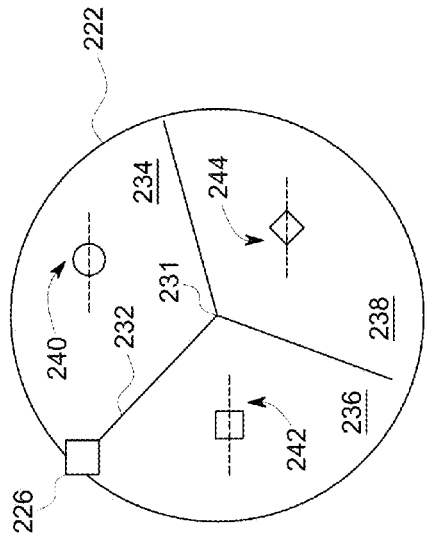
FIGS. 16-19 are schematic diagrams graphically illustrating a portion of the steps of the technique of FIG. 15 according to an embodiment of the invention.

Referring to FIGS. 15 and 18, upon a defining of each region 234, 236, 238, a center point or centroid is identified in each region at block 210, for each of the images acquired. According to one embodiment, the center point in each region for a first image acquired in the plurality of images can be selected as the reference center point from which shifts in position (of the center point) in subsequent images are determined, with the reference center point in the first image being chosen at diastole phase and fixed. Upon selection of the regional center points, a center point trajectory for each regional center point is then calculated at block 212 based on centroid movement in the corresponding binary mass(es). As shown in FIG. 18, a center point 240, 242, 244 (i.e., regional center points) is identified for each region 234, 236, 238, and a center point trajectory for each region is then calculated. Determining of the trajectories of center points 240, 242, 244 includes determining, for each center point, the differences in center point positions between respective consecutive base images (i.e., variances in position). These differences identify an amplitude or radial component of center point movement and an angle or circumferential component of center point movement. According to one embodiment, the center point trajectory can be mapped or plotted, with the plotting of the center point trajectories including plotting the distances (amplitudes) and directions (angles) of center point trajectory movement on polar coordinate maps, such as the polar coordinate map shown in FIG. 4, for example. A separate polar coordinate map plotting the distances (amplitudes) and directions (angles) of center point trajectory movement can be generated for each regional center point 240, 242, 244, with the plotting of amplitudes and angles of movement of the center points on such polar coordinate maps illustrating, for example, the extent, location, and pattern of ventricular wall contraction during systole and relaxation during diastole.

Figure 19:
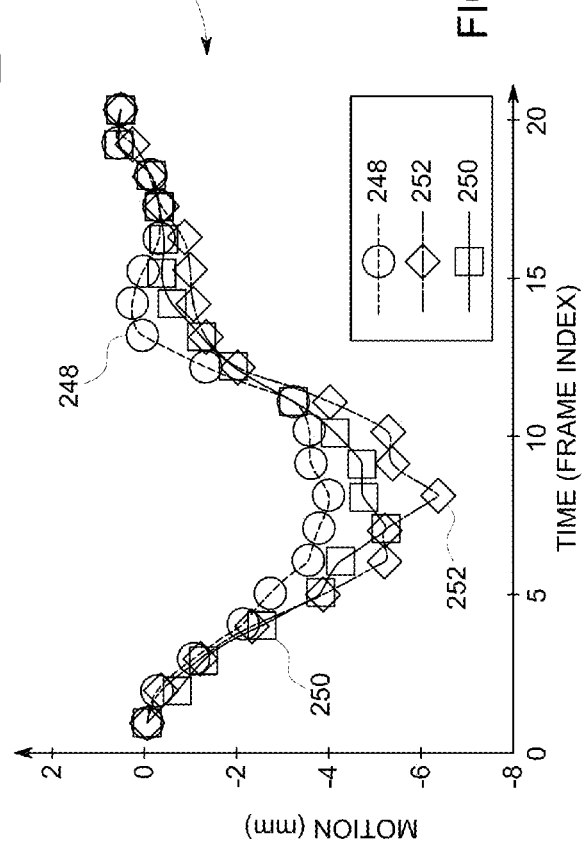

Upon calculation of the center point trajectory for each regional center point 240, 242, 244 across the plurality of images, the center point trajectory is decomposed into its radial and circumferential dimensions at block 214. The decomposition of the center point trajectory for each regional center point 240, 242, 244 into its radial and circumferential dimensions provides for the plotting of the radial motion as a function of time for each of the LAD, RCA and LCX regions at block 216, such that a radial trajectory/motion versus time plot is generated and displayed, such as the radial trajectory/motion versus time plot 246 shown in FIG. 19. As shown in FIG. 19, a separate radial trajectory/motion versus time curve is generated for each region, such that an LAD curve 248, an RCA curve 250, and an LCX curve 252 are provided. Beneficially, the ability to assess individual wall segment motion that is provided by FIG. 19 via curves 248, 250, 252 enables the evaluation of relative wall motion between regions, providing for a diagnosis of the patient that may be based on the relative wall motions, notably dysynchrony, a potentially treatable cause of heart failure. Additionally, a maximum radial motion of the center point in each region can be calculated/identified from the acquired images at block 218. Identification of the local maximum radial motion component can provide for an accurate diagnosis of diffused or global positive myocardial infarction patients, allowing for a distinction between such patients and normal/healthy subjects.

Figure 20:
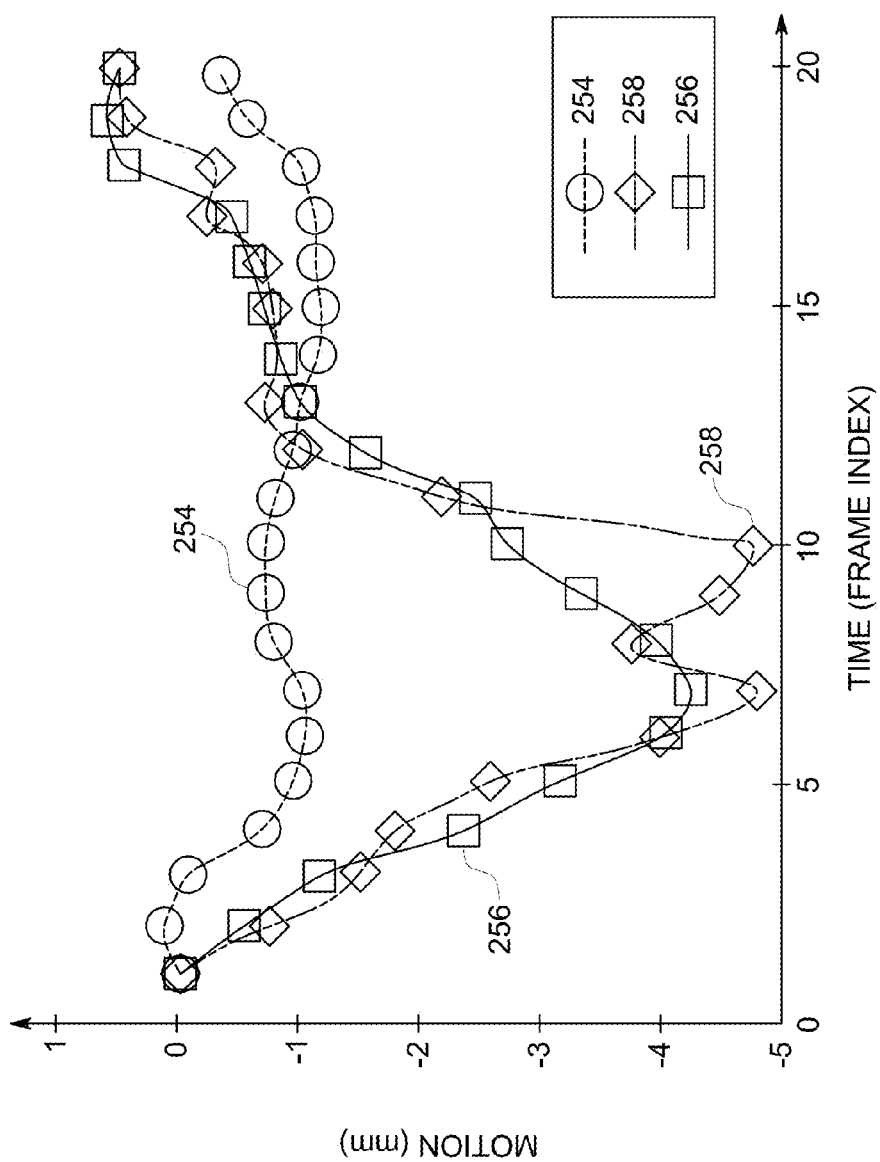
FIGS. 20-22 illustrate exemplary plots of patient data using radial motion versus time curves according to an embodiment of the invention.
Figure 21:
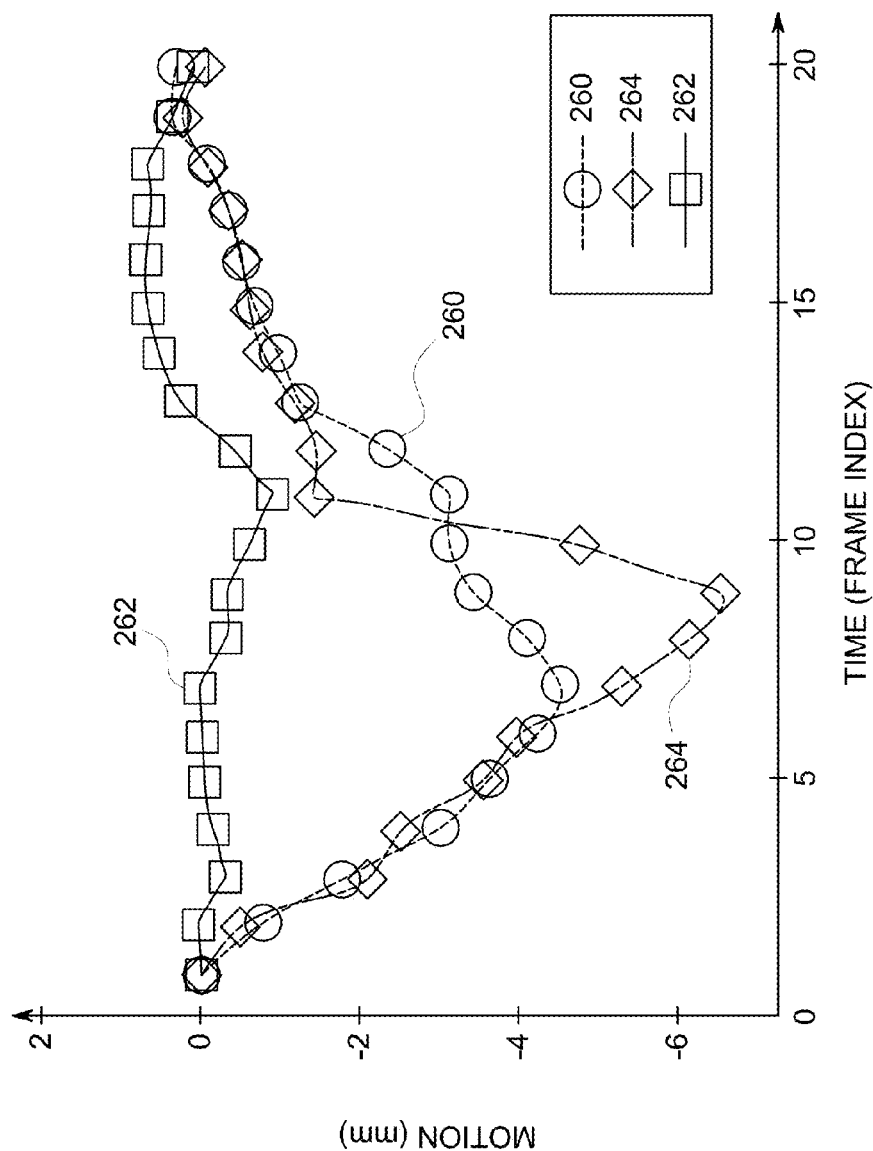
Figure 22:
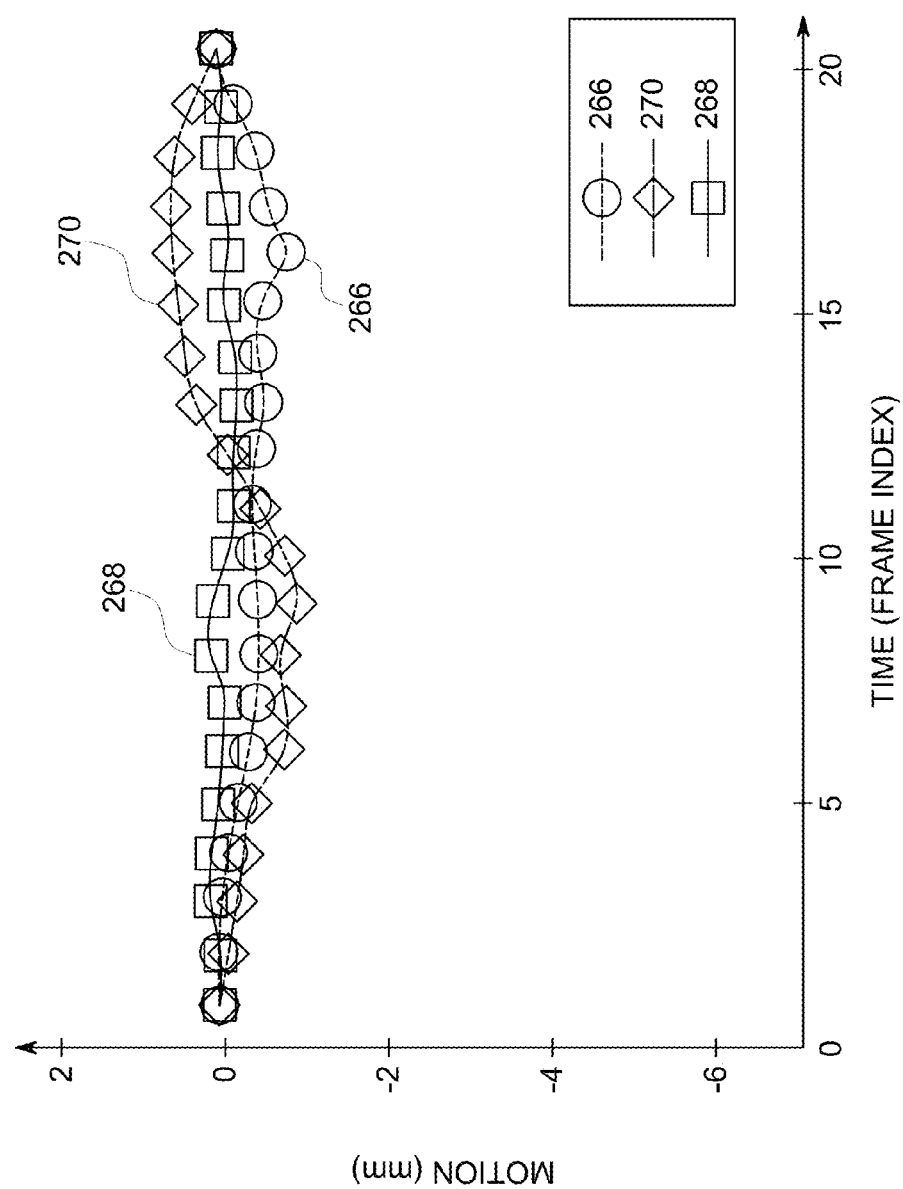

Examples of assessing ventricular wall motion for the LAD, RCA, and LCX regions for various subjects by way of the multi-segment CPT mapping technique 200 (FIG. 15) are shown in FIG. 19 and in FIGS. 20-22. With respect to FIG. 19, center point radial trajectory versus time curves are provided for a 47-year-old male volunteer with ejection fraction (EF) of 63%. As illustrated via curves 248, 250, 252, the LAD, RCA, and LCX regions show a consistent trend of center point radial motion across time, which illustrates a synchronized contraction of the respective ventricular wall segments. The maximum radial motion of the LAD, RCA, and LCX regions are 4.02 mm, 5.25 mm, 6.45 mm, respectively.

Referring now to FIG. 20, center point radial trajectory versus time curves are provided for a 63-year-old male patient with known chronic myocardial infarction in the LAD region with residual left ventricular dilation (68 mm) and reduced ejection fraction (39%). Center point radial motion in the LAD, RCA and LCX regions, as illustrated via curves 254, 256, 258, show that the LAD motion is not synchronized with the RCA motion and the LCX motion. Additionally, the LAD curve 254 shows that the ventricular wall in the LAD region has limited motion through the cardiac cycle, with the magnitude of the maximum radial motion in the LAD region being 1.21 mm, versus 4.83 mm and 4.28 mm in the LCX and RCA regions. The reduced LAD region radial motion indicates an abnormal wall motion region in the corresponding area of the anteroseptal and anterior regions, with the reduction in resting left ventricular function being associated with dyskinesis of the infarct regions.

Referring now to FIG. 21, center point radial trajectory versus time curves are provided for a 56-year-old male patient with positive myocardial infarction in basal inferoseptal area and with hypokinesis and reduced ejection fraction of 26%. Center point radial motion in the LAD, RCA and LCX regions, as illustrated via curves 260, 262, 264, show that the RCA motion is not synchronized with the LAD motion and the LCX motion. Additionally, the RCA curve 262 shows that the ventricular wall in the RCA region has limited motion through the cardiac cycle, with the magnitude of the maximum radial motion in the RCA region being 0.84 mm, versus 4.38 mm and 6.32 mm in LAD region and LCX region. The reduced RCA region radial motion indicates an abnormal wall motion region in the corresponding inferoseptal and inferior regions.

Referring now to FIG. 22, center point radial trajectory versus time curves are provided for the same 56-year-old male patient as shown in FIG. 21, but with an apical aneurysm of the left ventricle. Analysis of the LAD, RCA and LCX curves 266, 268, 270, shows a reduced motion in each of the LAD, RCA and LCX regions. The magnitude of the maximum radial motions in the LAD, RCA, and LCX regions is 0.80 mm, 0.19 mm, and 0.91 mm, respectively. The limited ventricular wall motion in each of the LAD, RCA, and LCX regions is consistent with chronic myocardial infarction and diffuse multi-vessel coronary artery disease.

Figure 23:
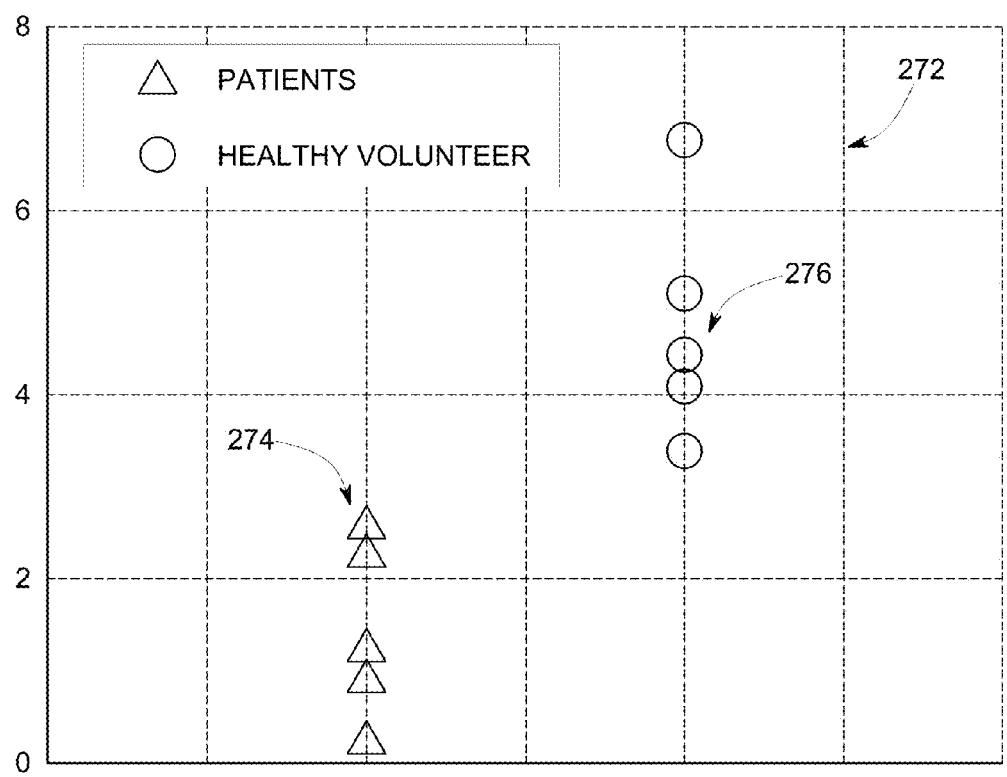
FIG. 23 illustrates exemplary plots of patient data using Welch two-sample t-test according to an embodiment of the invention.

FIG. 23 illustrates a plot 272 of patient data using a Welch two-sample t-test, with the y-axis representative of radial motion (mm). A first group of patient data 274 for patients with myodacdial infarction and wall motion abnormalities is illustrated together with a second group of patient data 276 for healthy subjects. Plot 272 illustrates data related to maximum radial motion in the LAD, RCA and LCX regions, with each data point representing a minimum value selected from the maximum radial motion values of the LAD, RCA and LCX regions for use in comparison. As illustrated, the patient data 276 for the healthy subjects has an average amplitude of 4.71+/−1.27 mm. The patient data 274 for patients with focal and global wall motion abnormality, however, has an average amplitude of 1.33+/−0.79 mm. Thus, the radial motion values of the patients with focal and global wall motion abnormality were found to be significantly different (p=0.0009) from that of the healthy subjects, with the healthy subjects having much more motion than the patients with focal and global wall motion abnormality.

It is recognized that the technique 200 as described above may be used to track multiple regional center points of images for other cardiac chambers besides the left ventricle (i.e., the right ventricle, the left atrium, or the right atrium). The technique 200 described above may also be used to track center points for ROIs of other hollow chambers such as an esophagus or a stomach of an imaging subject. In addition, it is contemplated that the ROIs may be of any cavity of an imaging subject or object in either a medical or a non-medical setting, including ROI cavities having an irregular shape. Furthermore, technique 200 may be varied according to steps and procedures described earlier. That is, for example, absolute (or raw), EF weighted, and/or chamber radius change weighted center point trajectories may be determined, as it can be understood that the EF and radius change weighted maps provide extra information for diagnosis for both regional and global wall motion abnormalities in addition to the information of the absolute map.

Finally, as described above, the base images having the desired ROIs may include images selected from any type of modality including: echocardiography images, radionuclide imaging images, magnetic resonance images, computed tomography images, x-ray images, or ultrasound images based on any type of scanning sequence or imaging parameter setup. It is contemplated that diagnosis of wall motion abnormalities can include the quantification of cavity wall motion abnormalities from one modality compared with the quantification of the cavity wall motion abnormalities from a different modality. Further, as center point measurements are quantitative, direct comparison of wall motion between different patients is also contemplated.

Thus, beneficially, the multi-segment CPT mapping technique 200 is employed to enable multi-segment cardiac chamber movement analysis for evaluation of discrete myocardial segments, such as in multiple coronary artery related regions (e.g., LAD, RCA, and LCX vascular regions). The multi-segment CPT mapping technique provides an automated approach for short axis cardiac wall motion analysis that provides regarding where (LAD, RCA, and LCX regions), how much (maximum radial motion amplitude), and when to the synchronization (peaks or valleys in radial motion versus time curves) regarding wall motion. The multi-segment CPT mapping technique can thus provide a quantitative and/or relative criterion of coronary artery disease related analysis and provide an indication of coronary artery disease in each specific branch. Additionally, the multi-segment CPT mapping technique also provides for conclusions/diagnoses to be made based on the relationship between the regional center point trajectory of each region. That is, the multi-segment CPT mapping technique allows for the assessment of individual wall segments so as to enable the evaluation of relative wall motion, notably dyssynchrony, a potentially treatable cause of heart failure. Furthermore, for global positive myocardial infarction, the multi-segment CPT mapping technique makes use of the local maximum radial motion component as criteria, to aid in formulating an accurate diagnosis.

A technical contribution for the disclosed method and apparatus is that it provides for a computer implemented mapping of center point trajectory movement for each of a plurality of regional center points of a cavity.

Therefore, according to an embodiment of the invention, a non-transitory computer readable storage medium includes a computer program comprising instructions, which when executed by a computer, cause the computer to acquire a plurality of images, identify a region-of-interest in each of the plurality of images, divide the region-of-interest into a plurality of distinct regions, and locate a regional center point for each of the plurality of regions in each of the plurality of images. The instructions further cause the computer to determine, for each regional center point, a center point trajectory based on variances in position of the center points from each other in the plurality of images, decompose the center point trajectory of each regional center point into radial and circumferential components so as to isolate radial component of the center point trajectory for each regional center point in each of the plurality of images, and based on the determined radial component for each regional center point in each of the plurality of images, display radial motion versus time curves for each regional center point.

According to another embodiment of the invention, a method for multi-segment chamber movement analysis includes obtaining a plurality of images of a region-of-interest including a chamber therein, dividing the chamber into a plurality of segments for each of the plurality of images, and locating a centroid of each segment of the chamber in each of the plurality of images. The method also includes tracking movement of the centroid in each respective segment across the plurality of images to determine a center point trajectory for each centroid, determining a radial motion for the centroid in each respective segment based on the center point trajectory, and displaying the radial motion for each centroid in each the plurality of images on a respective radial motion versus time curve.

According to yet another embodiment of the invention, a non-transitory computer readable storage medium includes a computer program comprising instructions, which when executed by a computer, cause the computer to obtain a plurality of images of a region-of-interest including a walled chamber therein, isolate the walled chamber in each of the plurality of images, divide the walled chamber into a plurality of segments for each of the plurality of images, and locate a regional center point of each of plurality of segments in each of the plurality of images. The instructions further cause the computer to determine, for each of the regional center points, a center point trajectory based on a positional relationship of the center points to each other in the plurality of images, determine a radial motion component of the center point trajectory for each of the regional center points in each of the plurality of images, and display the radial motion for each regional center point in each of the plurality of images on a respective radial motion versus time curve.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A non-transitory computer readable storage medium having stored thereon a computer program comprising instructions, which when executed by a computer, cause the computer to:
   acquire a plurality of images;
   identify a region-of-interest in each of the plurality of images;
   divide the region-of-interest into a plurality of distinct regions;
   locate a regional center point for each of the plurality of regions in each of the plurality of images;
   for each regional center point, determine a center point trajectory based on variances in position of the center points from each other in the plurality of images;
   decompose the center point trajectory of each regional center point into radial and circumferential components, so as to isolate radial component of the center point trajectory for each regional center point in each of the plurality of images; and
   based on the determined radial component for each regional center point in each of the plurality of images, display radial motion versus time curves for each regional center point.

2. The computer readable storage medium of claim 1 wherein the region-of-interest corresponds to a left ventricle.

3. The computer readable storage medium of claim 2 wherein the instructions that cause the computer to divide the region-of-interest cause the computer to:
   perform an endocardium segmentation to identify the left ventricle and the right ventricle;
   identify a reference point at a mid-point between hinged points of the left ventricle and the right ventricle;
   generate a division line between a center point of the left ventricle and the reference point between hinged points of the left ventricle and the right ventricle; and
   rotate the division line a specified angular amount to divide the left ventricle into the plurality of distinct regions.

4. The computer readable storage medium of claim 3 wherein the instructions that cause the computer to rotate the division line cause the computer to rotate the division line 120 degrees in each of a clockwise and counter clockwise position to divide the left ventricle into three distinct regions.

5. The computer readable storage medium of claim 4 wherein the three distinct regions comprise a left anterior descending artery (LAD) region, a right coronary artery (RCA) region, and a left circumflex coronary artery (LCX) region.

6. The computer readable storage medium of claim 1 having further instructions to cause the computer to identify a maximum radial motion for each regional center point from the radial motion versus time curves.

7. The computer readable storage medium of claim 1 having further instructions to cause the computer to, for each of the regional center points, plot the variances in position of the center points between consecutive images of the plurality of images onto a polar coordinate map.

8. The computer readable storage medium of claim 7 wherein the instructions that cause the computer to plot the variances cause the computer to plot distances and directions of the positions of the center points between consecutive images of the plurality of images.

9. The computer readable storage medium of claim 1 having further instructions to cause the computer to assess wall motion for each of the plurality of regions in the region-of-interest based on the center point trajectory of each regional center point.

10. The computer readable storage medium of claim 1 wherein the plurality of images is one of a plurality of echocardiography images, a plurality of radionuclide imaging images, a plurality of magnetic resonance images, a plurality of computed tomography images, a plurality of x-ray images, and a plurality of ultrasound images.

11. The computer readable storage medium of claim 1 wherein the regional center point from a first image in the plurality of images comprises a reference center point from which the variances in position are determined.

12. A method for multi-segment chamber movement analysis comprising:
- obtaining a plurality of images of a region-of-interest including a chamber therein;
- dividing the chamber into a plurality of segments for each of the plurality of images;
- locating a centroid of each segment of the chamber in each of the plurality of images;
- tracking movement of the centroid in each respective segment across the plurality of images to determine a center point trajectory for each centroid;
- determining a radial motion for the centroid in each respective segment based on the center point trajectory; and
- displaying the radial motion for each centroid in each the plurality of images on a respective radial motion versus time curve.

13. The method of claim 12 wherein the chamber comprises a selected cardiac chamber, and wherein dividing the chamber comprises:
- performing an endocardium segmentation to identify the selected cardiac chamber and another cardiac chamber;
- identifying a reference point at a mid-point between hinged points of the selected cardiac chamber and the another cardiac chamber;
- generating a division line between a center point of the selected cardiac chamber and the reference point; and
- dividing the selected cardiac chamber based on a location of the division line and on the number of segments in the cardiac chamber.

14. The method of claim 13 further comprising rotating the division line 120 degrees in each of a clockwise and counter clockwise position to divide the cardiac chamber into three distinct segments, wherein the selected cardiac chamber comprises the left ventricle and wherein the three distinct regions comprise a left anterior descending artery (LAD) region, a right coronary artery (RCA) region, and a left circumflex coronary artery (LCX) region.

15. The method of claim 12 further comprising determining a maximum radial motion for the centroid in each respective segment from the radial motions for each centroid across the plurality of images.

16. The method of claim 12 further comprising mapping the center point trajectory for the centroid in each respective segment onto a polar coordinate map.

17. A non-transitory computer readable storage medium having stored thereon a computer program comprising instructions, which when executed by a computer, cause the computer to:
- obtain a plurality of images of a region-of-interest including a walled chamber therein;
- isolate the walled chamber in each of the plurality of images;
- divide the walled chamber into a plurality of segments for each of the plurality of images;
- locate a regional center point of each of plurality of segments in each of the plurality of images;
- for each of the regional center points, determine a center point trajectory based on a positional relationship of the center points to each other in the plurality of images;
- determine a radial motion component of the center point trajectory for each of the regional center points in each of the plurality of images; and
- display the radial motion for each regional center point in each of the plurality of images on a respective radial motion versus time curve.

18. The computer readable storage medium of claim 17 wherein the walled chamber comprises a selected cardiac chamber, and wherein the instructions that cause the computer to divide the walled chamber cause the computer to:
- perform an endocardium segmentation to identify the selected cardiac chamber and another cardiac chamber;
- identify a reference point at a mid-point between hinged points of the selected cardiac chamber and the another cardiac chamber;
- generate a division line between a center point of the selected cardiac chamber and the reference point; and
- divide the selected cardiac chamber based on a location of the division line and on the number of segments in the cardiac chamber.

19. The computer readable storage medium of claim 18 having further instructions to cause the computer to rotate the division line 120 degrees in each of a clockwise and counter clockwise position to divide the selected cardiac chamber into three distinct regions, wherein the segments comprise a left anterior descending artery (LAD) region, a right coronary artery (RCA) region, and a left circumflex coronary artery (LCX) region.

20. The computer readable storage medium of claim 17 having further instructions to cause the computer to calculate a maximum radial motion for each regional center point from the radial motions of the regional center points across the plurality of images.

* * * * *